US006316639B1

(12) United States Patent
Fritz-Langhals

(10) Patent No.: US 6,316,639 B1
(45) Date of Patent: Nov. 13, 2001

(54) PROCESS FOR THE PREPARATION OF CYCLIC N-HYDROXYDICARBOXIMIDES

(75) Inventor: Elke Fritz-Langhals, Ottobrunn (DE)

(73) Assignee: Consortium für elektrochemische Industrie GmbH, München (DE)

( * ) Notice: Subject to any disclaimer, the term of this patent is extended or adjusted under 35 U.S.C. 154(b) by 0 days.

(21) Appl. No.: 09/657,201

(22) Filed: Sep. 7, 2000

(30) Foreign Application Priority Data

Sep. 7, 1999 (DE) .............................. 199 42 700

(51) Int. Cl.⁷ ................................. C07D 207/46
(52) U.S. Cl. ............................................... 548/542
(58) Field of Search ............................... 548/542

(56) References Cited

U.S. PATENT DOCUMENTS

| 4,709,025 | 11/1987 | Mewshaw et al. | 540/335 |
| 5,332,637 | 7/1994 | Wilson et al. | 430/106.6 |
| 5,872,261 | 2/1999 | Bremmer | 548/542 |

FOREIGN PATENT DOCUMENTS

| 1051170 | 5/1991 | (CN) . |
| 130680 | 4/1902 | (DE) . |
| 35 24 808 | 1/1987 | (DE) . |
| 19723890 | 12/1998 | (DE) . |
| 19723961 | 12/1998 | (DE) . |
| 0251994 | 1/1988 | (EP) . |
| 0664479 | 7/1995 | (EP) . |
| 0810318 | 5/1997 | (EP) . |
| 2 178 427 | 2/1987 | (GB) . |
| 6-301168 | 1/1994 | (JP) . |
| 95/25090 | 9/1995 | (WO) . |

OTHER PUBLICATIONS

English Derwent Abstract AN 1999–036065[04] corresponding to DE 19723961.
English Derwent Abstract AN 1999–036040[04] corresponding to DE 19723890.
English Derwent Abstract AN 1995–036040[04] corresponding to JP 6–301168.
English Derwent Abstract AN 1988–001825[01] corresponding to EP 0251994.
H. Gross and I. Keitel,, J. Prakt. Chem. 1969, 311 p. 692–693.
K. Kurita, H. Imajo and Y. Iwakura, J. Polymer Science A–1, 17, p. 1619–1629.
L. F. Fieser and M. Fieser, "Reagents for Organic Synthesis", Wiley New York, 1967, p. 485–486.
A. Rougny and M. Daudon, Bull. Soc. Chim. Fr. 1976, p. 833–838.
English Chemical Abstract corresponding to CN 1051170.

*Primary Examiner*—Amelia Owens
(74) *Attorney, Agent, or Firm*—Collard & Roe, P.C.

(57) ABSTRACT

The invention discloses a process for the preparation of cyclic N-hydroxydicarboximides, involving reacting a dicarboxylic acid or anhydride thereof with a salt of hydroxylamine in solution without the further addition of a base.

19 Claims, No Drawings

PROCESS FOR THE PREPARATION OF CYCLIC N-HYDROXYDICARBOXIMIDES

BACKGROUND OF THE INVENTION

1) Field of the Invention

The invention relates to a process for the preparation of cyclic N-hydroxydicarboximides.

2) Background Art

N-Hydroxydicarboximides are used widely in industry. For example, they are used in the synthesis of organic compounds. EP-A 664479 and JP-A 06301168 disclose the use of N-hydroxyphthalimide as oxidizing agents in photographic developers. U.S. Pat. No. 5,332,637 describes the use of N-hydroxyphthalimide in toners.

N-Hydroxyphthalimide is also used widely for the synthesis of O-substituted hydroxylamines, which are frequently used for the formation of the oxime in pharmacologically effective compounds and compounds effective as pesticides.

EP-A 25199, EP-A 810318 and U.S. Pat. No. 4,709,025 disclose processes for the preparation of highly antibacterially effective O-substituted aminoxy or iminoxy compounds, in particular, from the group of betalactams, using N-hydroxyphthalimide.

WO 95/25090 describes the use of N-hydroxydicarboximides as initiators in polymerization reactions. DE-A 19723961 and DE-A 19723890 disclose that N-hydroxyphthalimide and derivatives thereof can also be used for selective oxidation reactions.

For the synthesis of cyclic N-hydroxydicarboximides, the corresponding dicarboxylic anhydride and a hydroxylammonium salt, for example, hydroxylammonium chloride or hydroxylammonium sulfate, have hitherto always been used with the addition of a base.

L. F. Fieser and M. Fieser, "Reagents for Organic Synthesis", Wiley N.Y., 1967, pp. 485–486 and K. Kurita, H. Imajo and Y. Iwakura, J. Polym. Science A-1 1979, 17, 1619–1629 propose, for example, the synthesis of N-hydroxyphthalimide using pyridine as the base.

DE-A 130680, H. Gross and I. Keitel, J. Prakt. Chem. 1969, 311, 692–693 and CN-A 1051170 disclose the syntheses of cyclic N-hydroxydicarboximides using hydroxylamine hydrochloride in aqueous solution, with sodium carbonate serving as the base.

A. Rougny and M. Daudon, Bull. Soc. Chim. Fr. 1976, 833–838 describe a synthesis route of N-hydroxyphthalimide in which sodium acetate is used as the base.

WO 95/25090 discloses a process for the preparation of cyclic N-hydroxyimides using sodium hydroxide as the base.

It is a considerable disadvantage that in the case of all of the processes described, salts are formed during the synthesis which have to be subsequently disposed of as waste products. Moreover, free hydroxylamine is difficult to handle and for this reason is not used. An additional disadvantage of the processes described is that only the dicarboxylic anhydrides, and not the free dicarboxylic acids, can be used since the latter are rapidly deactivated via the acid/base reaction.

The object was therefore to find a process for the preparation of cyclic N-hydroxydicarboximides which does not require the addition of a base and therefore does not have the disadvantages of the prior art.

SUMMARY OF THE INVENTION

The invention provides a process for the preparation of cyclic N-hydroxydicarboximides, which comprises reacting dicarboxylic acids or anhydrides thereof with a salt of hydroxylamine in solution without the further addition of a base. In the process according to the invention, the corresponding dicarboxylic acids or anhydrides thereof are reacted with a salt of hydroxylamine.

The salts of hydroxylamine are compounds of the general composition

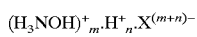

where m is 1, 2 or 3, n is 0, 1 or 2, with the proviso that m+n=1, 2 or 3, and X is a phosphate, sulfate, nitrate, halide, acetate, trifluoroacetate, trichloroacetate, tetrafluoroborate or sulfonate $R^Y SO_3^-$.

The radical $R^Y$ is a $C_1$–$C_3$-alkyl, phenyl or 4-methylphenyl group. The salts of hydroxylamine can also be used in the form of their hydrates.

In the process according to the invention, preference is given to using salts of hydroxylamine from the group consisting of hydroxylammonium phosphate, hydroxylammonium sulfate, hydroxylammonium chloride and hydroxylammonium trifluoroacetate.

The reaction of the dicarboxylic acids or the dicarboxylic anhydrides is carried out with 1 to 5 equivalents, preferably with 1 to 2 equivalents, of the hydroxylammonium salt at temperatures between 60° C. and 180° C., preferably 80° C. to 150° C., and particularly preferably, 100° C. to 140° C.

Solvents which may optionally be added are water or inert solvents, for example aliphatic or aromatic hydrocarbons, alcohols, chlorinated hydrocarbons or ethers or else mixtures thereof. The amount of solvent here is between 10% and 5000%, based on the hydroxylammonium salt used.

Preferred solvents are water, methanol, ethanol, ligroin, benzene, toluene, nitrobenzene, xylene or methyl tert-butyl ether.

The reaction times are 10 min to 10 hours, preferably 1 hour to 6 hours.

The dicarboxylic anhydrides used, or the dicarboxylic acids obtainable therefrom by the addition of water, are preferably compounds which contain at least one five- or six-membered ring. The ring can be substituted or unsubstituted.

Particularly preferred dicarboxylic anhydrides are compounds having the general formulae Ia, Ib, Ic and Id.

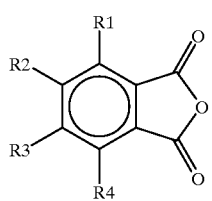

Ia

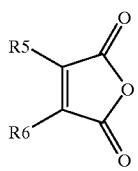

Ib

-continued

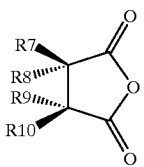
Ic

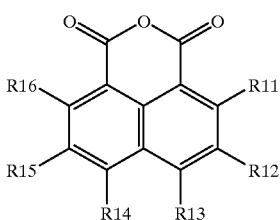
Id

Particularly preferred free dicarboxylic acids are compounds having the general formulae IIa, IIb, IIc and IId.

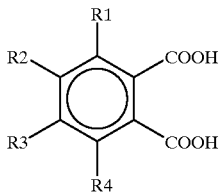
IIa

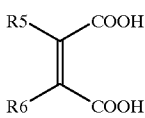
IIb

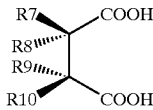
IIc

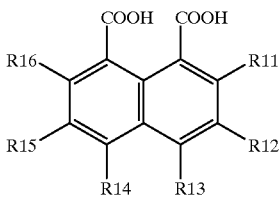
IId

The radicals $R^1$ to $R^{16}$ can be identical or different and can be a halogen radical, carboxyl radical, salt or ester of a carboxyl radical, hydrogen, hydroxyl, formyl, carbamoyl, sulfono radical, ester or salt of the sulfono radical, sulfamoyl, nitro, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono, phosphonooxy radical, ester or salt of the phosphonooxy radical.

The carbamoyl, sulfamoyl, amino and phenyl radicals can be unsubstituted or mono- or polysubstituted by a further radical $R^{17}$.

The aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl radicals can be saturated or unsaturated, branched or unbranched and can be mono- or polysubstituted by a further radical $R^{17}$.

This radical $R^{17}$ can be identical or different and can be a hydroxyl, formyl, carboxyl radical, ester or salt of the carboxyl radical, carbamoyl, sulfono radical or salt of the sulfono radical, sulfamoyl, nitro, amino, phenyl, $C_1$–$C_5$-alkyl, $C_1$–$C_5$-alkoxy radical.

The radicals $R^7$ and $R^8$ or $R^9$ and $R^{10}$ must not be a hydroxyl or amino radical at the same time.

In each case, two of the substituents $R^1$ to $R^4$, $R^5$ to $R^6$, $R^7$ to $R^{10}$ and/or $R^{11}$ to $R^{16}$, can each be linked to a radical —E—, where —E— has one of the four following meanings:

—(—CH═CH—)$_n$— where n=1 to 3 or —CH═CH—CH═N—

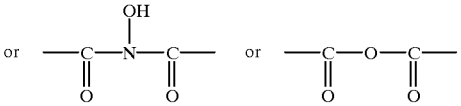

The radicals $R^7$ to $R^{10}$ can also be connected to one another by one or two bridging elements —F—, where —F— is identical or different and is —O—, —S—, —CH$_2$— or —$CR^{18}$═$CR^{19}$—. The radicals $R^{18}$ and $R^{19}$ can be identical or different and have the meaning of $R^1$.

The cyclic N-hydroxydicarboximides obtained by the process of the invention are preferably compounds of the general structure which contain at least one five- or six-membered ring. The ring can be substituted or unsubstituted.

Particularly preferred N-hydroxydicarboximides are compounds having the general formulae IIIa, IIIb, IIIc and IIId.

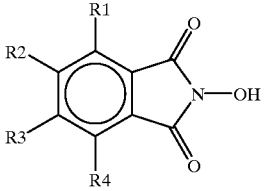
IIIa

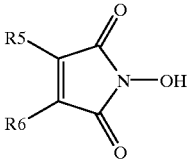
IIIb

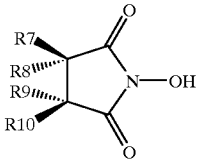
IIIc

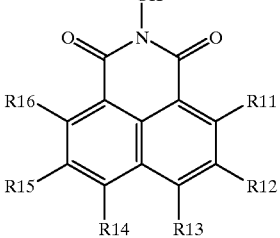
IIId

Examples of compounds of the formula IIIa are N-hydroxyphthalimide and substituted N-hydroxyphthalimide derivatives, such as 3-amino-N-hydroxyphthalimide, 4-amino-N-hydroxyphthalimide, 3-methyl-N-hydroxyphthalimide, 4-methyl-N-hydroxyphthalimide, N-hydroxybenzene-1,2,4-tricarboxylic acid imide, N,N'-dihydroxybenzophenone-3,3',4,4'-tetracarboxylic acid diimide or N,N'-dihydroxypyromellitic acid bisimide.

Examples of compounds of the formula IIIb are N-hydroxymaleimide and substituted N-hydroxymaleimide derivatives, such as pyridine-2,3-dicarboxylic acid N-hydroxyimide, N-hydroxynaphthalic acid imide and optionally, substituted N-hydroxynaphthalic acid imide derivatives.

Examples of compounds of the formula IIIc are N-hydroxysuccinimide and optionally, substituted N-hydroxysuccinimide derivatives, such as, for example, N-hydroxytartaric acid imide, N-hydroxy-5-norbornene-2,3-dicarboxylic acid imide, exo-N-hydroxy-7-oxabicyclo[2.2.1]hept-5-ene-2,3-dicarboximide, N-hydroxy-cis-cyclohexane-1,2-dicarboximide and N-hydroxy-cis-4-cyclohexene-1,2-dicarboxylic acid imide.

Examples of compounds of the formula IIId are N-hydroxynaphthalene-1,8-dicarboxylic acid imide, N,N'-dihydroxynaphthalene-1,4,5,8-tetracarboxylic acid diimide and N,N'-dihydroxyperylene-3,4,9,10-tetra-carboxylic acid diimide.

The examples below serve to illustrate the invention further.

EXAMPLE 1

Preparation of N-hydroxyphthalimide 1.48 g (10.0 mmol) of phthalic anhydride and 0.723 g (3.67 mmol) of hydroxylammonium phosphate were pulverized, mixed and, following the addition of 2 ml of water, heated at a bath temperature of 130° C. for about 1½ hours. The cooled lemon-yellow reaction mixture was diluted with water, and the solid was filtered off with suction, washed with water and dried at 50° C. The yield was 1.39 g (86%).

EXAMPLE 2

Preparation of N-hydroxyphthalimide 0.15 g (1.0 mmol) of phthalic anhydride was mixed with 0.2 to 1 equivalent of hydroxylammonium sulfate (see Table 1) and, optionally after the addition of water (see Table 1), heated to 130° C. in a sealed ampoule. The reaction times were varied for the individual mixtures in accordance with Table 1. The cooled reaction mixture was dissolved in $d_6$-DMSO and analyzed using $_1$H-NMR spectroscopy. The yields are given in each case in Table 1.

TABLE 1

Reaction of phthalic anhydride with hydroxyl-ammonium sulfate as in Example 2

| Equivalents $(H_3NOH)_2SO_4$[a] | Equivalents $H_2O$[a] | Reaction time (h) | Yield (%) HPI[b] |
|---|---|---|---|
| 0.2 | 0 | 6 | 44 |
| 0.2 | 0 | 14.5 | 31 |
| 0.2 | 0.1 | 3 | 42 |
| 0.2 | 0.1 | 6 | 50 |
| 0.2 | 0.1 | 14.5 | 45 |
| 0.4 | 0 | 6 | 34 |
| 0.4 | 0 | 14.5 | 41 |
| 0.4 | 0.2 | 3 | 31 |
| 0.4 | 0.2 | 6 | 30 |

TABLE 1-continued

Reaction of phthalic anhydride with hydroxyl-ammonium sulfate as in Example 2

| Equivalents $(H_3NOH)_2SO_4$[a] | Equivalents $H_2O$[a] | Reaction time (h) | Yield (%) HPI[b] |
|---|---|---|---|
| 0.4 | 0.2 | 14.5 | 52 |
| 0.6 | 0 | 6 | 31 |
| 0.6 | 0 | 14.5 | 45 |
| 0.6 | 0.3 | 3 | 25 |
| 0.6 | 0.3 | 6 | 37 |
| 0.6 | 0.3 | 14.5 | 26 |
| 0.8 | 0 | 6 | 43 |
| 0.8 | 0 | 14.5 | 49 |
| 0.8 | 0.4 | 3 | 32 |
| 0.8 | 0.4 | 6 | 31 |
| 0.8 | 0.4 | 14.5 | 32 |
| 1.0 | 0 | 6 | 37 |
| 1.0 | 0 | 14.5 | 34 |
| 1.0 | 0.5 | 3 | 30 |
| 1.0 | 0.5 | 6 | 30 |
| 1.0 | 0.5 | 14.5 | 29 |

[a] based on phthalic anhydride used
[b] based on N-hydroxyphthalimide used

EXAMPLE 3

Preparation of 3-hydroxy-N-hydroxy-phthalimide 500 mg (3.05 mmol) of 3-hydroxyphthalic anhydride and 240 mg (1.22 mmol) of hydroxylammonium phosphate were mixed and heated with 1 ml of water at a bath temperature of 130° C. for 3 hours. The cooled reaction mixture was digested in water, filtered off with suction and dried. The yield was 495 mg (91%).

m.p. 238–239° C. (decomp.), $^1$H-NMR (CDCl$_3$+DMSO): δ=7.19–7.30 (m, 2H), 7.47–7.59 (mc, 1H), 10.44 (s, broad, OH), $^1$H-NMR (CDCl$_3$): δ=7.19 (m, 1H), 7.30 (m, 1H), 7.44–7.50 (mc, 1H), 9.24 (s, broad, OH), 10.40 (s, broad, OH), IR (KBr): 3440 m, 3150 w, 1760 w, 1700 s, 1620 m cm$^{-1}$.

EXAMPLE 4

Preparation of 4-methyl-N-hydroxyphthalimide 500 mg (3.08 mmol) of 4-methylphthalic anhydride and 243 mg (1.23 mmol) of hydroxylammonium phosphate were mixed and heated with 1 ml of water at a bath temperature of 130° C. for 3 hours. The cooled mixture was digested with 30 ml of water. The precipitate which formed was filtered off with suction and dried at 60° C. under reduced pressure. The yield was 437 mg (80%).

m.p. 175–176° C. (decomp.), $^1$H-NMR (DMSO): δ=2.48 (s, CH$_3$), 7.58–7.80 (m, 3H), 10.77 (s, broad, OH).

EXAMPLE 5

Preparation of 4-nitro-N-hydroxyphthalimide

Analogous to Example 4, but from 500 mg (2.37 mmol) of 4-nitrophthalic acid (tech., contaminated with approximately 10% of 3-nitrophthalic acid) and 187 mg (0.974 mmol) of hydroxylammonium phosphate at a bath temperature of 130° C. The yield was 332 mg (67%, approximately 5% contaminated).

Melting range 101–110° C. (decomp.). $^1$H-NMR (DMSO): δ=8.05–8.12 (m, 1H), 8.42–8.49 (m, 1H), 8.59–8.68 (m, 1H).

EXAMPLE 6

Preparation of 3-nitro-N-hydroxyphthalimide

Analogous to Example 4, but from 500 mg (2.37 mmol) of 3-nitrophthalic acid and 187 mg (0.947 mmol) of hydroxylammonium phosphate at a bath temperature of 130° C. The yield was 443 mg (90%).

Decomposition from 90° C., $^1$H-NMR (DMSO): δ=8.00–8.15 (m, 2H), 8.22–8.31 (m, 1H).

EXAMPLE 7

Preparation of 3-amino-N-hydroxyphthalimide 1.81 g (10.0 mmol) of 3-aminophthalic acid (purity 90%) and 0.721 g (3.66 mmol) of hydroxylammonium phosphate were pulverized, mixed and, with 2 ml of water, heated at a bath temperature of about 130° C. for 3 hours. The cooled reaction mixture was slurried with a small amount of acetonitrile and filtered off with suction. The yield was 1.87 g (quantitative).

m.p. 247–249° C. (decomp.), $^1$H-NMR (DMSO): δ=6.90–7.00 (m, 2H), 7.39–7.46 (m, 1H), IR (KBr): 3470 m, 3380 s, 3180 w, 1770 w, 1710 s, 1640 m, 1585 w cm$^{-1}$.

EXAMPLE 8

Preparation of N-hydroxynaphthalene-1,8-dicarboxylic acid imide 1.98 g (10.0 mmol) of 1,8-naphthalenedicarboxylic anhydride and 0.985 g (5.00 mmol) of hydroxylammonium phosphate were reacted with 2 ml of water analogously to Example 7 for 6 hours at a bath temperature of 130° C. Following cooling, the pale brown reaction mixture was digested with water, and the solid was filtered off with suction and dried. The yield was 1.89 g (89%).

Decomposition from 269° C., $^1$H-NMR (DMSO): δ=7.84–7.93 (m, 2H), 8.42–8.53 (m, 4H), 10.76 (s, broad, OH).

EXAMPLE 9

Preparation of bis-N,N'-dihydroxy-pyromellitic acid imide 2.18 g (10.0 mmol) of pyromellitic dianhydride and 3.28 g (20.0 mmol) of hydroxylammonium sulfate were mixed and, with 4 ml of water, were heated firstly for 3 hours at a bath temperature of 90° C. and then for a further 9 hours at a bath temperature of 110° C. Analysis by $^1$H-NMR spectroscopy revealed a conversion of about 36%. $^1$H-NMR (DMSO): δ=8.1 (s, aromat. H)

I claim:

1. A process for the preparation of cyclic N-hydroxy-dicarboximides, which comprises reacting dicarboxylic acids or anhydrides thereof with a salt of hydroxyl-amine in solution without the further addition of a base; and wherein th e salt of hydroxylamine ha s the general composition

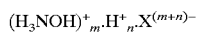

where m is 1, 2 or 3, n is 0, 1 or 2, with the proviso that m+n=1, 2 or 3, and X is at least one member selected from the group consisting of phosphate, sulfate, nitrate, acetate, trifluoroacetate, trichloroacetate, tetrafluoroborate and sulfonate R$^y$SO$^{31}$$_3$, wherein R$^y$ is C$_1$–C$_3$-alkyl, phenyl or 4-methylphenyl.

2. The process as claimed in claim 1, wherein the dicarboxylic anhydrides are compounds having at least one, optionally substituted, a five- or six-membered ring, comprising the general structure

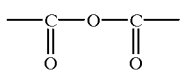

or the dicarboxylic acid formed therefrom by the addition of water.

3. The process as claimed in claim 1, wherein dicarboxylic anhydrides having the general formulae Ia, Ib, Ic and Id or the acids corresponding thereto are selected from the group

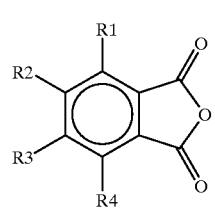

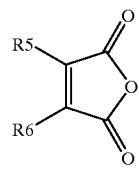

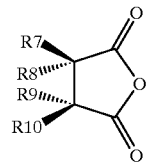

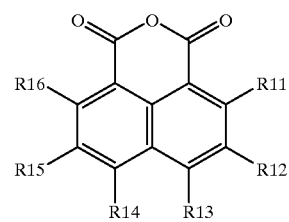

wherein the R$^1$ to R$^{16}$ radicals can be identical or different and are selected from the group consisting of hydrogen, halogen, hydroxyl, carboxyl, a salt or ester of carboxyl, formyl, carbamoyl, sulfono, ester or salt of sulfono, sulfamoyl, nitro, amino, phenyl, aryl-C$_1$–C$_5$-alkyl, C$_1$–C$_{12}$-alkyl, C$_1$–C$_5$-alkoxy, C$_1$–C$_{10}$-carbonyl, carbonyl-C$_1$–C$_6$-alkyl, phospho, phosphono, phosphonooxy, and ester or salt of phosphonooxy; wherein the carbamoyl, sulfamoyl, amino and phenyl radicals can be unsubstituted or mono- or polysubstituted by R$^{17}$ wherein R$^{17}$ can be identical or different and is selected rom the group consisting of hydroxyl, formyl, carboxyl, ester or salt of carboxyl, carbamoyl, sulfono radical or salt of the sulfono radical, sulfamoyl, nitro, amino, phenyl, C$_1$–C$_5$-alkyl and C$_1$–C$_5$alkoxy, wherein the aryl-C$_1$–C$_5$-alkyl, C$_1$–C$_{12}$-alkyl, C$_1$–C$_5$-alkoxy, C$_1$–C$_{10}$-carbonyl, carbonyl-C$_1$–C$_6$-alkyl radicals can be saturated or unsaturated, branched or unbranched and can be mono- or poly substituted by R$^{17}$ as hereinbefore defined, and wherein R$^7$ and R$^8$, or R$^9$ and R$^{10}$ are not hydroxyl or amino at the same time.

4. The process as claimed in claim 3, wherein the carbamoyl, sulfamoyl, amino and phenyl radicals are unsubstituted.

5. The process as claimed in claim 3, wherein the aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl radicals are saturated or unsaturated, branched or unbranched and are unsubstituted.

6. The process as claimed in claim 3, wherein in each case two of the substituents $R^1$ to $R^4$, $R^5$ to $R^6$, $R^7$ to $R^{10}$ and/or $R^{11}$ to $R^{16}$ are linked to a radical —E—, where —E— is selected from the group consisting of:

(—CH=CH—)$_n$ where n=1 to 3 or
—CH=CH—CH=N—,

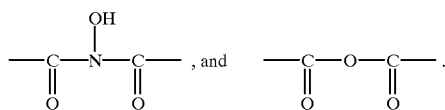

7. The process as claimed in claim 3, wherein the radicals $R^7$ to $R^{10}$ are connected to one another by one or two bridging elements —F—, where —F— is identical or different and is —O—, —S—, —CH$_2$— or —CR$^{18}$=CR$^{19}$—, wherein $R^{18}$ and $R^{19}$ are identical or different and have the meaning of $R^1$.

8. The process as claimed in claim 1, wherein the salts of hydroxylamine are used in the form of their hydrates.

9. The process as claimed in claim 1, wherein at least one salt of hydroxylamine is selected from the group consisting of hydroxylammonium phosphate, hydroxylammonium sulfate, and hydroxylammonium trifluoroacetate.

10. The process as claimed in claim 1, wherein the reaction is carried out at a temperature between 60° C. and 180° C.

11. The process as claimed in claim 10, further comprising a solvent; and
wherein the solvent used is one or more substances selected from the group consisting of water, aliphatic hydrocarbons, aromatic hydrocarbons, alcohols, chlorinated hydrocarbons and ethers.

12. The process as claimed in claim 11, wherein the solvent is at least one of the substances selected from the group consisting of water, methanol, ethanol, ligroin, benzene, toluene, nitrobenzene, xylene and methyl tert-butyl ether.

13. The process of claim 3 wherein the cyclic N-hydroxydicarboximide is N-hydroxyphthalimide.

14. The process of claim 3 wherein the cyclic N-hydroxydicarboximide is 3-hydroxy-N-hydroxyphthalimide.

15. The process of claim 3 wherein the cyclic N-hydroxydicarboximide is 4-methyl-N-hydroxyphthalimide.

16. The process of claim 3 wherein the cyclic N-hydroxydicarboximide is 4-nitro-N-hydroxyphthalimide.

17. The process of claim 3 wherein the cyclic N-hydroxydicarboximide is 3-amino-N-hydroxyphthalimide.

18. The process of claim 3 wherein the cyclic N-hydroxydicarboximide is N-hydroxynaphthalene-1,8-dicarboxylic acid imide.

19. The process of claim 3 wherein the cyclic N-hydroxydicarboximide is bis-N,N$^1$-dihydroxypyromellitic acid imide.

* * * * *